United States Patent
Watanabe et al.

(10) Patent No.: US 9,140,675 B2
(45) Date of Patent: Sep. 22, 2015

(54) TEST SYSTEM

(71) Applicant: HORIBA, Ltd., Kyoto (JP)

(72) Inventors: Koji Watanabe, Kyoto (JP); Hiroshi Nakamura, Kyoto (JP); Kaoru Okada, Kyoto (JP); Masayuki Hayata, Kyoto (JP); Toru Yamazaki, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 0 days.

(21) Appl. No.: 13/672,995

(22) Filed: Nov. 9, 2012

(65) Prior Publication Data

US 2013/0124033 A1 May 16, 2013

(30) Foreign Application Priority Data

Nov. 10, 2011 (JP) .................................. 2011-246282
May 23, 2012 (JP) .................................. 2012-118095

(51) Int. Cl.
*G01N 33/00* (2006.01)
*G01M 15/10* (2006.01)
(Continued)

(52) U.S. Cl.
CPC ......... *G01N 33/0004* (2013.01); *G01M 15/102* (2013.01); *G01M 17/0072* (2013.01); *G01N 33/00* (2013.01); *G01N 33/0006* (2013.01); *G01N 33/0009* (2013.01); *G07C 5/00* (2013.01); *G07C 5/006* (2013.01)

(58) Field of Classification Search
CPC .............. G01N 33/00; G01N 33/0004; G01N 33/0006; G01N 33/0031; G01N 33/0009
USPC ............ 701/29.4, 33.4, 115, 29.1, 32.8–34.4, 701/102, 108; 702/22–24, 33–36, 182–187, 702/FOR. 135; 73/23.2–23.36, 115.01, 73/115.02, 116.06, 118.01, 116.01, 73/116.05, 116.07, 862–862.382
See application file for complete search history.

(56) References Cited

U.S. PATENT DOCUMENTS 3,973,848 A * 8/1976 Jowett et al. ..................... 356/51
4,125,894 A * 11/1978 Cashel et al. ................. 701/123
4,160,373 A * 7/1979 Fastaia et al. ................ 73/23.31
(Continued)

FOREIGN PATENT DOCUMENTS

| JP | 03225089 | 10/1991 |
| JP | 2000310643 | 11/2000 |

(Continued)

OTHER PUBLICATIONS

HORIBA Automotive Test Systems, No. HRA-2248C, MEXA7000 Version 3, Sep. 2010, Japan, 40 pages.
(Continued)

*Primary Examiner* — Thomas Tarcza
*Assistant Examiner* — Tyler J Lee
(74) *Attorney, Agent, or Firm* — Brooks Kushman P.C.

(57) ABSTRACT

According to the present invention, a test system 1 that tests a mobile body such as a vehicle, a vessel, and a plane, or an instrument used in the mobile body as an object, and is operable by switching among different operational modes, can accumulate an operating period of a component much more accurately than conventional system, and includes an accumulated operating-time calculating unit 46 for accumulating the operating time of the component, and the accumulated operating-time calculating unit 46 accumulates the operating time of the component only in the predetermined operational mode.

9 Claims, 10 Drawing Sheets

(51) Int. Cl.
*G01M 17/007* (2006.01)
*G07C 5/00* (2006.01)

(56) References Cited

U.S. PATENT DOCUMENTS

| | | | | |
|---|---|---|---|---|
| 4,215,404 A * | 7/1980 | Bukhtiyarov et al. | ......... | 701/102 |
| 4,328,546 A * | 5/1982 | Kreft et al. | ..................... | 701/102 |
| 4,800,378 A * | 1/1989 | Putrow et al. | ..................... | 345/10 |
| 5,245,324 A * | 9/1993 | Jonker et al. | ............... | 345/440.1 |
| 5,267,542 A * | 12/1993 | Keskula | ................... | 123/406.65 |
| 5,355,713 A * | 10/1994 | Scourtes et al. | ........... | 73/114.76 |
| 5,435,192 A * | 7/1995 | Eagan et al. | ................ | 73/116.05 |
| 5,705,742 A * | 1/1998 | Fox et al. | ................... | 73/114.79 |
| 6,085,154 A * | 7/2000 | Leuthausser et al. | ........... | 702/34 |
| 6,112,151 A * | 8/2000 | Kruse | ........................... | 701/115 |
| 6,269,292 B1 * | 7/2001 | Kokubu et al. | ............... | 701/29.6 |
| 6,285,947 B1 * | 9/2001 | Divljakovic et al. | ........... | 701/110 |
| 6,459,969 B1 * | 10/2002 | Bates et al. | .................. | 701/31.4 |
| 6,601,441 B1 * | 8/2003 | Torgerson et al. | ......... | 73/116.06 |
| 6,721,649 B2 * | 4/2004 | Knott et al. | .................... | 701/114 |
| 7,231,285 B2 * | 6/2007 | Noguchi | .......................... | 701/33.4 |
| 7,308,614 B2 * | 12/2007 | Kojori | ........................... | 714/47.2 |
| 7,424,351 B2 * | 9/2008 | Noguchi | ....................... | 701/33.4 |
| 7,636,648 B2 * | 12/2009 | Johansson et al. | ............. | 702/184 |
| 7,660,652 B2 * | 2/2010 | Smith et al. | .................. | 701/31.5 |
| 8,032,279 B2 * | 10/2011 | Rogers et al. | ................. | 701/36 |
| 8,131,495 B2 * | 3/2012 | Krafthefer et al. | ............. | 702/104 |
| 8,473,176 B2 * | 6/2013 | Youngquist et al. | .......... | 701/101 |
| 8,494,810 B2 * | 7/2013 | Goldfine et al. | ............. | 702/183 |
| 8,533,018 B2 * | 9/2013 | Miwa et al. | .................. | 705/7.13 |
| 2004/0150674 A1 * | 8/2004 | Takahashi et al. | ............ | 345/810 |
| 2005/0043869 A1 * | 2/2005 | Funkhouser et al. | ........... | 701/29 |
| 2008/0110238 A1 * | 5/2008 | Kariya et al. | ................ | 73/23.31 |
| 2008/0307772 A1 * | 12/2008 | Kawamura et al. | ............. | 60/285 |
| 2009/0157252 A1 * | 6/2009 | Saen et al. | ...................... | 701/33 |
| 2010/0324376 A1 * | 12/2010 | Chinnadurai et al. | ........ | 600/300 |

FOREIGN PATENT DOCUMENTS

| | | |
|---|---|---|
| JP | 2000310643 A | 11/2000 |
| JP | 2003-149099 A | 5/2003 |
| JP | 2003294763 | 10/2003 |
| JP | 2004045347 | 2/2004 |
| JP | 2005-049353 A | 5/2005 |
| JP | 2005348837 | 12/2005 |
| JP | 2009210318 | 9/2009 |
| JP | 2010156649 A | 7/2010 |

OTHER PUBLICATIONS

Hiroshi Kawamura, Automotive Development and Progress in Horiba's Emission Measurement Technologies, Readout, No. 34, Jan. 31, 2009, Japan, 12 pages.

Hideki Ohashi, et al., Motor Exhaust Gas Analyzer MEXA-7000 Series 1. Product Concept, Readout, No. 11, Sep. 8, 1995, Japan, 7 pages.

Kenji Takeda, et al., Motor Exhaust Gas Analyzer MEXA-7000 Series 2. Downsizing and Modular Configuration of Analyzers, Readout, No. 11, Sep. 8, 1995, Japan, 7 pages.

Kaoru Okada, Motor Exhaust Gas Analyzer MEXA-7000 Series 3. Data Processing System and Communications Line, Readout, No. 11, Sep. 8, 1995, Japan, 9 pages.

* cited by examiner

FIG. 8

| Item Name | Warning | Period | Unit | Count mode | Elapsed | Count Reset |
|---|---|---|---|---|---|---|
| Linearization | ✓ | 0 | Hours | Always | 715 | Reset |
| CO2 Interference | | 0 | Days | Always | 99 | Reset |
| NOx Efficiency | | 0 | Days | Always | 48 | Reset |
| Leak Check | ✓ | 8 | Days | Always | 41 | Reset |
| HC Hangup Check | | 0 | Days | Always | 25 | Reset |
| CLA Quenching Check | | 0 | Days | Always | 25 | Reset |
| HC Relative Response | | 0 | Days | Always | 48 | Reset |
| CO2 Interference[CFR] | | 0 | Days | Always | — | Reset |
| NOx Efficiency[CFR] | | 0 | Days | Always | 39 | Reset |

Maintenance Caution — W1

Line / Common — B6

Item Setup — B1    OK — B7    CANCEL — B8

Maintenance Caution

Line  Common

| Item Name | Warning | Period | Unit | Count mode | Elapsed | Count Reset |
|---|---|---|---|---|---|---|
| Leak Check[CFR] | ☐ | 0 | Days | Always | 41 | Reset |
| HC Hangup Check[CFR] | ☐ | 0 | Days | Always | 39 | Reset |
| CLA Quenching Check[CFR] | ☐ | 0 | Days | Always | 19 | Reset |
| HC Relative Response[CFR] | ☐ | 0 | Days | Always | 39 | Reset |
| CO2 Interference[CFR] | ✓ | 0 | Days | Always | --- | Reset |
| T.P | ☐ | 0 | Hours | Always | 115 | Reset |
| MCU | ☐ | 0 | Hours | Always | 115 | Reset |
| User Definition 1 | ☐ | 0 | Hours | None | 0 | Reset |
| User Definition 2 | ☐ | 0 | Hours | None | 0 | Reset |

Item Setup  OK  CANCEL

FIG.10

| Item Name | Warning | Period | Unit | Count mode | Elapsed | Count Reset |
|---|---|---|---|---|---|---|
| MCU | ☐ | 0 | Hours | Always | 115 | Reset |
| User Definition 1 | ☐ | 0 | Hours | None | 0 | Reset |
| User Definition 2 | ☐ | 0 | Hours | None | 0 | Reset |
| User Definition 3 | ☐ | 0 | Hours | None | 0 | Reset |
| User Definition 4 | ☐ | 0 | Days | None | 0 | Reset |
| User Definition 5 | ☐ | 0 | Days | None | 0 | Reset |
| User Definition 6 | ☐ | 0 | Days | None | 0 | Reset |
| User Definition 7 | ☐ | 0 | Days | None | 0 | Reset |
| User Definition 8 | ☐ | 0 | Days | None | 0 | Reset |

Maintenance Caution

Line — Common

Item Setup | OK | CANCEL

TEST SYSTEM

CROSS-REFERENCE TO RELATED APPLICATION

This application claims priority to Japanese Application No. 2012-118095 filed May 23, 2012, and Japanese Application No. 2011-246282 filed Nov. 10, 2011, the disclosures of which are incorporated in their entirety by reference herein.

FIELD

The present invention relates to a test system for mobile bodies such as vehicles, vessels, and planes, and also for testing components of the mobile bodies, for example, an internal-combustion engine.

BACKGROUND

A known conventional automobile test system is configured such that a plurality of measuring apparatuses (measuring devices) are connected to one measurement managing device, and the managing device manages the measuring apparatuses together.

SUMMARY

The measuring device operates in various operational modes including an elapsed mode in which an embedded PC is in a conducting state, a stand-by mode in which measurement can be immediately started, a measurement mode, a calibration mode, a purge mode, and a measurement+purge mode. The measuring device includes various components such as a valve, a pump, a sensor, and a heater. For this reason, depending on the operational mode of the measuring device, some components actually operate, while other components do not actually operate. Accordingly, even in the operational mode in which some components do not actually operate, when operating periods of the components are uniformly accumulated, the operating periods of the components cannot be accurately accumulated. Further, it has been demanded to manage the timing of operational check such as leak check and purge processing of an exhaust gas flow line constituting a test system such as an exhaust-gas analyzing system.

The present invention is made in consideration of such problem, and its main object is to acquire operating history of instruments constituting the test system or operational check history of the test system as well as to accumulate the operating period of each component much more accurately than the conventional system.

That is, a test system according to the present invention is a test system that tests a mobile body such as a vehicle, a vessel or a plane, or instruments used in the mobile body as objects, and is operable by switching among different operational modes, the test system including a history-information acquiring unit for acquiring operating history information indicating operating history including operating time of a component or operational check history information indicating operational check history of operational check, wherein, in accumulating the operating time of the component, the history-information acquiring unit accumulates the operating time of the component only in the predetermined operational mode set for each component.

With such configuration, by accumulating the operating time of each component only in the predetermined operational mode set for each component, the accumulation of the operating period of each component can be performed much more accurately than conventional system.

As a specific implementation, preferably, one or more testing devices used for testing, and a device-managing device communicably connected to the testing devices, the device-managing device managing the testing devices, are further included, an accumulated operating-time calculating unit accumulates the operating time of components of the testing devices, and the device-managing device includes an accepting unit for accepting designation of the component and designation of the predetermined operational mode of the designated component.

Even when the testing device is connected to any device-managing device, for the device-managing device to accurately accumulate the operating time of the testing device, it is preferred that the device-managing device is provided with an accumulated operating-time calculating unit, and the testing device is provided with an accumulated operating-time storing unit for storing accumulated operating time calculated by the accumulated operating-time calculating unit.

To generate warnings in two stages and improve usability, it is preferred that the device-managing device further includes a warning generating unit for generating a real warning when the accumulated operating time reaches lifetime of the component, and a preliminary warning when the accumulated operating time reaches a predetermined time prior to the lifetime. To set the lifetime and/or the predetermined time, it is preferred to provide an accepting unit for accepting designation of the lifetime and/or the predetermined time.

As a specific implementation, it is desired that the testing devices are measuring devices for measuring a state amount of the object, and more specifically, the measuring device is provided in an exhaust path of the internal-combustion engine to measure the exhaust gas flowing through the exhaust path.

In the above-mentioned test system, the operating history of the instrument or the operational check history of the test system can be acquired, and furthermore, the user can arbitrarily set the instrument or the operational check, the history of which is to be acquired, to simplify management of the test system. The managing device used in the test system according to the present invention includes a display control unit displaying a setting screen for setting an instrument with operating history to be managed among the instruments constituting the test system such as the exhaust-gas analyzing system or setting operational check of the test system with operational check history to be managed, and a history-information acquiring unit for acquiring operating history information indicating the operating history of the instrument set on the setting screen, or operational check history information indicating the operational check history of the operational check set on the setting screen.

With such configuration, since the history-information acquiring unit acquires the operating history information of the instrument set on the setting screen or the operational check history information of the operational check set on the setting screen, the operating history information of the instruments constituting the test system such as the exhaust-gas analyzing system or the operational check history information of the operational check can be managed, and further, the user can arbitrarily set the instrument or operational check to be managed. Therefore, according to the present invention, the user can arbitrarily select the instrument or operational check to be managed and therefore, management of the exhaust-gas analyzing system can be simplified.

It is desired that the operating history information includes the accumulated operating time of the instrument, and the operational check history information includes elapsed time from completion of the last operational check. Since the operating history information includes the accumulated operating time, the state of the instruments constituting the test system can be easily recognized, and for example, the usable life and maintenance timing of the instruments can be easily managed. Further, since the operational check history information includes the elapsed time from completion of the last operational check, the timing of next operational check can be estimated.

Desirably, the setting screen has an upper limit value input column for setting an upper limit value of the accumulated operating time of the set instrument or the elapsed time of the set operational check, and the test system further includes a time comparing unit for comparing the upper limit value set by the upper limit value input column with the accumulated operating time or elapsed time acquired by the history-information acquiring unit, and an informing unit for informing that the accumulated operating time or the elapsed time exceeds the upper limit value. Thus, since the user merely inputs the upper limit value in the upper limit value input column on the setting screen, thereby having the device automatically compare the upper limit value with the accumulated operating time or the elapsed time, the user does not need to confirm the accumulated operating time or the elapsed time each time, which improves usability.

It is desired that the display control unit displays the operating history information or the operational check history information, which is acquired by the history-information acquiring unit, on the setting screen. Thus, in setting the instrument or operational check to be managed on the setting screen, since setting can be changed with reference to the history, the usability in setting can be improved. Further, the numerical value inputted to the upper limit value input column can be visually compared with the accumulated operating time or the elapsed time.

A test system managing program according to the present invention allows a computer to perform functions of a display control unit for displaying a setting screen for setting an instrument with operating history to be managed among the instruments constituting the test system such as the exhaust-gas analyzing system or for setting operational check of the test system with operational check history to be managed, and a history-information acquiring unit for acquiring operating history information of the instrument set on the setting screen, or operational check history information of the operational check set on the setting screen.

According to the present invention thus configured, by accumulating the operating time of each component only in the predetermined operational mode set for each component, the accumulation of the operating period of each component can be performed much more accurately than conventional system.

BRIEF DESCRIPTION OF THE DRAWINGS

FIG. 8 is a diagram showing a setting screen in the second embodiment;

FIG. 9 is a diagram showing the setting screen in the second embodiment; and

FIG. 10 is a diagram showing the setting screen in the second embodiment.

DESCRIPTION OF EMBODIMENTS

1. First Embodiment

A first embodiment of the present invention will be described below with reference to drawings.

Figure 1:
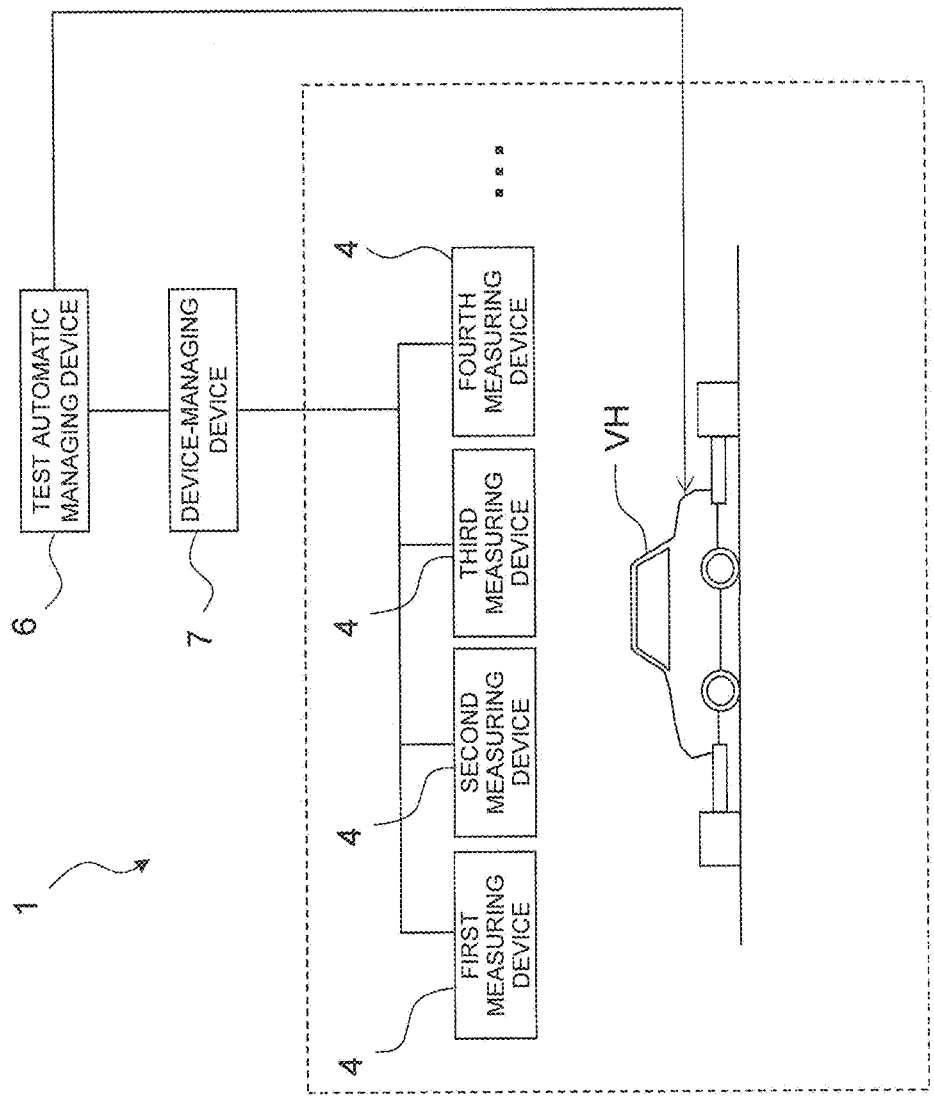
FIG. 1 is a schematic configuration diagram showing vehicle performance test system in accordance with a first embodiment of the present invention.

FIG. 1 schematically shows the whole of a vehicle performance test system 1 in accordance with the first embodiment. As shown in this diagram, the vehicle performance test system 1 includes a chassis dynamometer (not shown), an automatic driving device (not shown), a test automatic managing device 6, a plurality of exhaust-gas measuring devices 4, a device-managing device 7 and so on, and can test vehicle performances by putting a vehicle VH into a simulated driving state on the chassis dynamometer and measuring fuel consumption, exhaust-gas ingredients and so on of the vehicle VH. An engine as a single item can be tested. Each part will be described below.

Although not described in detail, the test automatic managing device 6 has a basic function of setting schedule of a driving test. When the operator performs such schedule setting, the test automatic managing device 6 transmits a command following its regulation to the chassis dynamometer, the automatic driving device, the device-managing device 7 and so on, and controls these components such that a test as regulated is automatically performed.

Although one device-managing device 7 is connected to one test automatic managing device 6 in FIG. 1, a plurality of the device-managing devices 7 may be connected. The test automatic managing device 6 can perform scheduling for each of the device-managing devices 7.

The exhaust-gas measuring device 4 (hereinafter, may be also referred to as measuring device 4) includes an exhaust-gas ingredient measuring device configured of a set of one or more gas analyzing units as unit instruments and also, for example, a device that performs pre-processing of measuring exhaust-gas ingredients, for example, a constant-volume sampling device.

In this embodiment, plural types of measuring devices 4 are used. Examples include a first measuring device 4 that includes a plurality of gas analyzing units having different measurement principles, a second measuring device 4 as a constant-volume sampling device, a third measuring device 4 as an EGR rate measuring device, and a fourth measuring device 4 as an ultrasonic flow meter. Examples of the gas analyzing unit include FID that measures THC, and CLD that measures $NO_x$, and an NDIR that measures $CO_2$.

Figure 2:
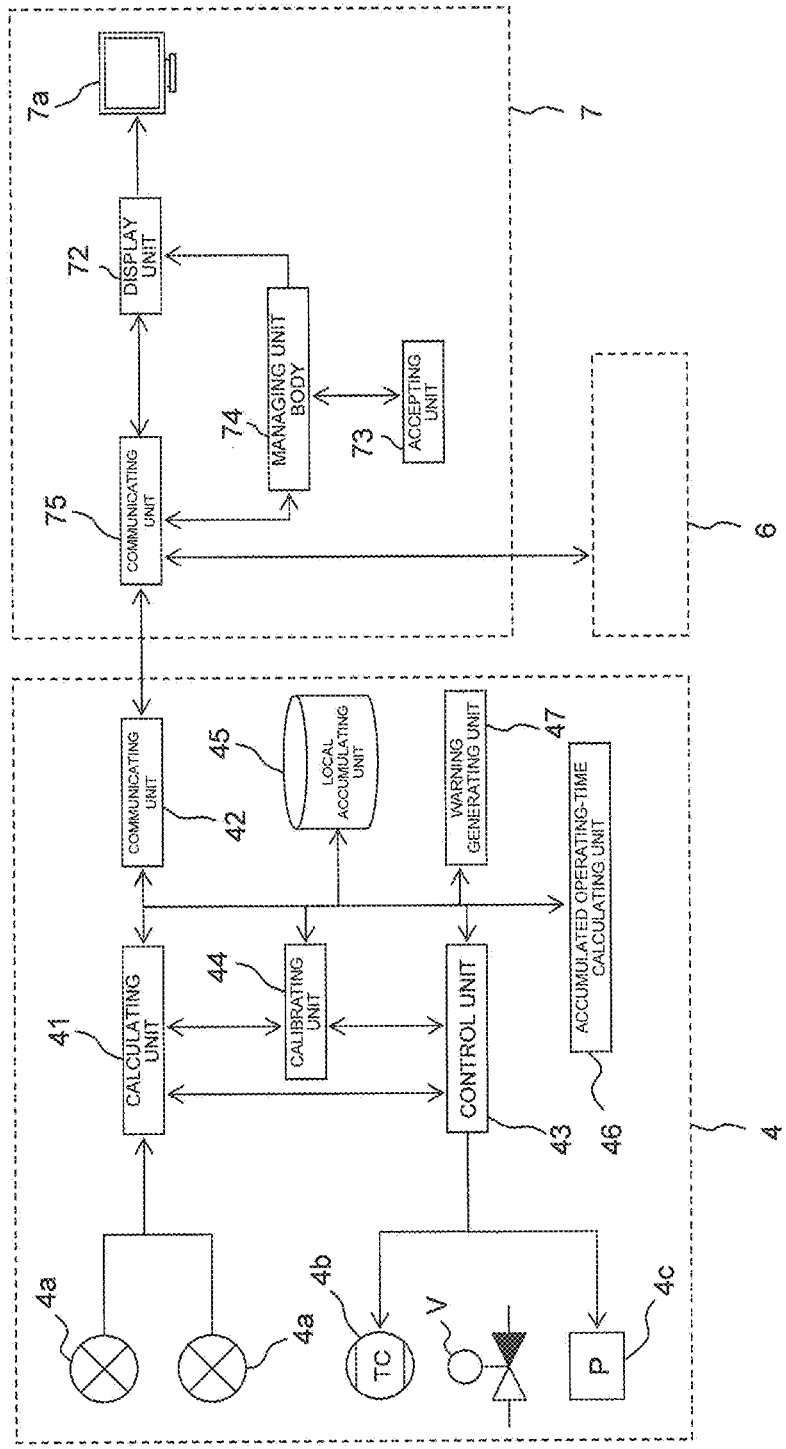
FIG. 2 is a functional block diagram of a measuring device and a device-managing device in the first embodiment.

The measuring device 4 measures the amount of ingredients such as HC, $NO_x$, CO, $CO_2$ of gas sampled from, for example, a predetermined place in an intake and exhaust path of an internal-combustion engine, and can also calculate performance values such as fuel consumption and EGR rate of the instruments constituting the vehicle VH such as engine and catalyst from the measured value. For this reason, each measuring device 4, as shown in FIG. 2, includes a local computer.

The local computer physically includes a CPU, a memory, an A/D converter, a communication interface and so on. In the local computer, the CPU and peripheral instruments work together according to a program stored in the memory and correct/calibrate an output value from a sensor 4a for detecting predetermined ingredients of exhaust gas, thereby calculating a measured value indicating the concentration of each of the ingredients. The local computer includes a calculating unit 41 that calculates a performance value of the instrument from the measured value and a communicating unit 42 that transmits the measured value and the instrument performance value, which are calculated by the calculating unit 41, to the device-managing device 7 according to a predetermined protocol.

The local computer further includes a control unit 43 that receives a command signal from the device-managing device 7 to control a valve V, a temperature regulating mechanism 4b, and a pump 4c, and controls the various operational modes (elapsed mode, stand-by mode, measurement mode, calibration mode, purge mode) of the exhaust-gas measuring device 4, a calibrating unit 44 that calibrates the sensor 4a, a local accumulating unit (accumulated operating-time storing unit) 45 that is provided in a predetermined area of the memory and successively acquires and accumulates device state information of the measuring device 4 up to now, an accumulated operating-time calculating unit 46 as a history-information acquiring unit, and a warning generating unit 47.

The device-managing device 7 is configured, for example, by installing a predetermined program in a general-purpose computer, and physically includes a CPU, a memory, a display, an input means (keyboard, mouse and the like), and a communication interface. The CPU and peripheral instruments work together according to the program stored in the memory, resulting in that the device-managing device 7, as shown in FIG. 2, performs functions of a display unit 72, an accepting unit 73, a managing unit body 74, and a communicating unit 75. The device-managing device 7 is provided with a communications port, and the measuring device 4 is intercommunicated with the device-managing device 7 by wired or wireless connection.

Figure 3:
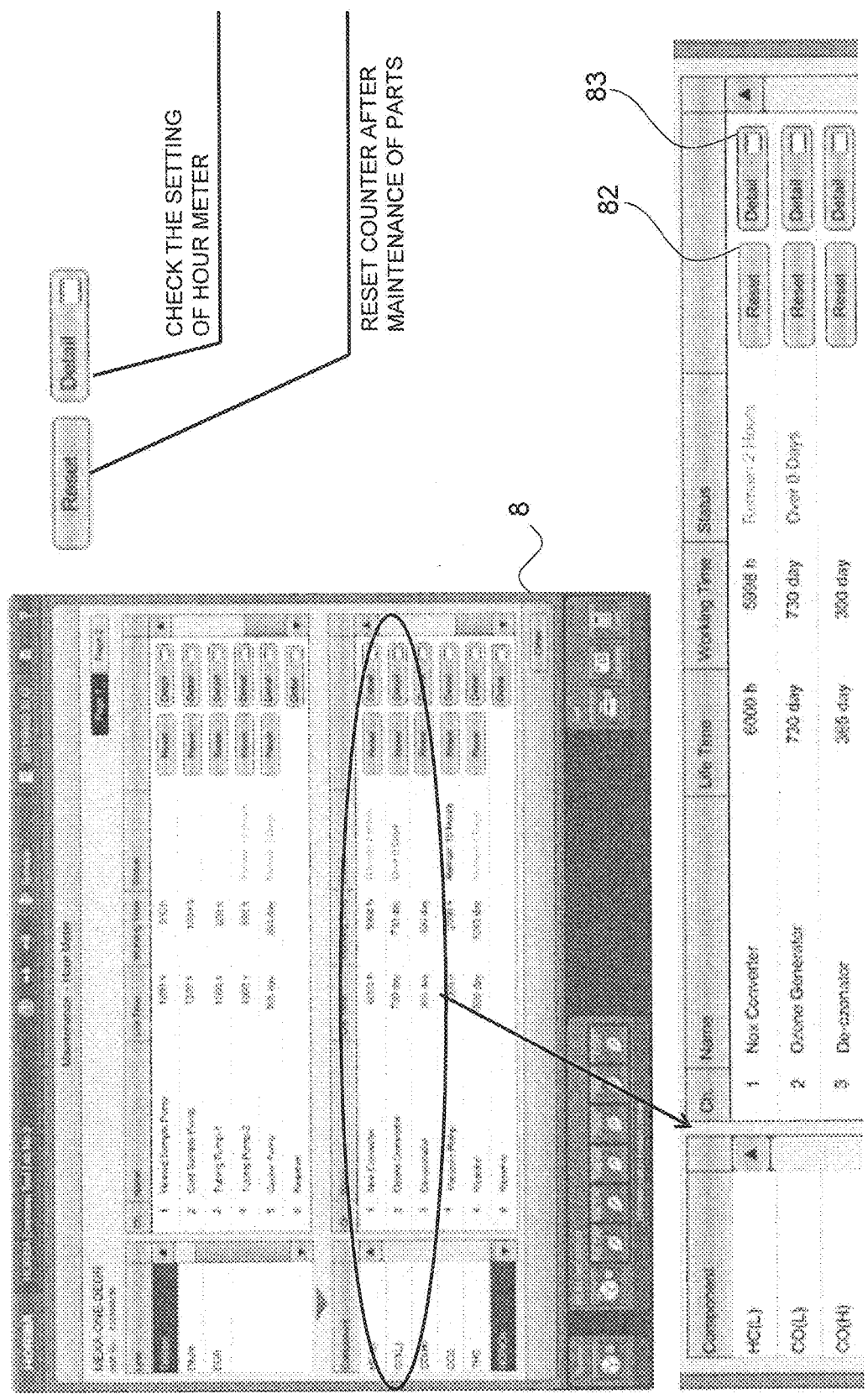
FIG. 3 is a screen configuration view showing an example of a warning screen in the first embodiment.

Next, each unit of the device-managing device 7 and their operations will be described. First, the operator performs various operations (for example, piping) related to the measuring device 4 and then, physically connects the measuring device 4 to the device-managing device 7 with a connector cable. In this state, the operator can properly display a warning screen 8 in a window as shown in FIG. 3.

A list of names of the components of the measuring device 4 is displayed on the warning screen 8. For each component, the list includes a name column as well as a life column "Life Time", an accumulated operating time column "Working Time" indicating the accumulated operating time up to now, and a remaining time column "Status" indicating remaining time to the end of life.

The remaining time column also indicates below-mentioned warning. Specifically, when the accumulated operating time reaches lifetime of the component, the warning generating unit 47 generates a red real warning. When the accumulated operating time reaches a predetermined preliminary warning period prior to the lifetime, an orange preliminary warning is displayed. In this manner, in this embodiment, two-staged warning display is carried out. On the warning screen, a "Reset" button 82 is operated, for example, after completion of maintenance of each component to reset the accumulated operating time.

Figure 4:
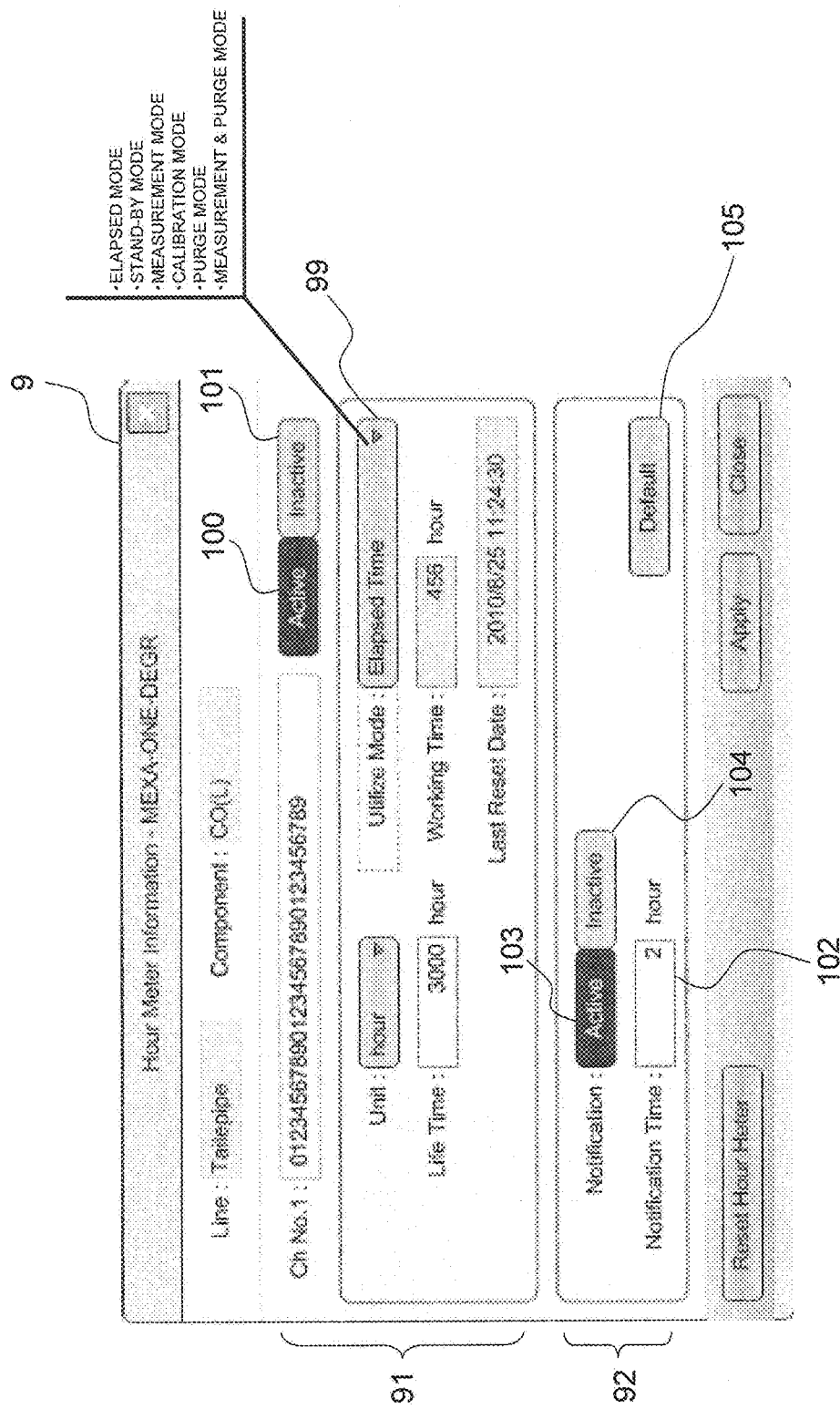
FIG. 4 is a screen configuration view showing an example of a setting screen in the first embodiment.

The list on the warning screen 8 is also provided with a "Detail" button 83 as a detail setting button in each row (that is, each component). When the Detail button 83 is clicked, a setting screen 9 for setting the life, the accumulated operating time and so on of each component is displayed in the window. Specifically, as shown in FIG. 4, the setting screen 9 includes an operational mode designating area 91 and a warning period designating area 92.

The operational mode designating area 91 includes various columns for designating whether or not the operating time of each component is accumulated when the measuring device 4 is put into each operating mode. Specifically, the columns are a mode designating column 99 for designating the operational mode, a finalizing button 100 for finalizing the designation, and a release button 101 for releasing the designation.

For example, in the case where the component operates only in the stand-by mode and the measurement mode, the operator may click the finalizing button 100 in the state where the stand-by mode is selected and displayed in the mode designating column 99, click the finalizing button 100 in the state where the measurement mode is selected and displayed in the mode designating column 99, and click the release button 101 each time each of the other modes is displayed in the mode designating column 99. By clicking the finalizing button 100, operating condition information, that is, information that time is accumulated only in the stand-by mode and the measurement mode is associated with a component ID and stored in the local accumulating unit 45 of the measuring device 4.

The accumulated operating-time calculating unit 46 acquires the operating condition information from the local accumulating unit 45, and keeps time by use of a timer not shown only in the operational mode indicated by the operating condition information to accumulate the operating time of the component. The accumulated operating time is successively written into the local accumulating unit 45. Hour Meter as the timer may be attached to the measuring device 4, and the accumulated operating-time calculating unit 46 may operate the Hour Meter only in the operational mode, and calculate the accumulated operating time from an output from the Hour Meter. Examples of the component include a pump, an ozone generator used to measure $NO_x$ by use of a CLD meter, and a filter as consumable supplies.

The warning period designating area 92 includes a display column 102 for displaying the preliminary warning period, buttons 103, 104 for validating/invalidating warning display, and a default button 105 for setting the preliminary warning period to a default value, and the setting can be changed by operator's inputting. When being finalized, these values are associated with the component ID and stored in the local accumulating unit 45.

In this embodiment thus configured, by accumulating the operating time of each component of the measuring device 4 only in the predetermined operational mode set for each component, the accumulation of the operating period of the component can be performed much more accurately than conventional system.

Further, by storing the accumulated operating time calculated by the accumulated operating-time calculating unit 46 in the local accumulating unit 45, even when the measuring device 4 is connected to any device-managing device, the device-managing device can accurately accumulate the operating time of the measuring device 4. Furthermore, the warning generating unit 47 allows the two-staged warning display on the warning screen 8, thereby improving usability.

Further, since the device-managing device 7 includes the accepting unit 73 that accepts designation of the lifetime and/or the predetermined time, the operator can flexibly set the lifetime or the predetermined time.

The present invention is not necessarily applied to only the first embodiment. For example, the present invention can be applied to testing of the engine as a single item, as well as planes, vessels and instruments thereof.

In the above-mentioned embodiment, the test automatic managing device 6 transmits the command following the regulation to the chassis dynamometer, the automatic driving device, and the device-managing device 7 to control these components such that the test can be automatically performed as scheduled. However, the present invention is not limited to this. For example, the device-managing device 7 may transmit the command following the regulation to each measuring device 4, and for example, the local computer built in the measuring device 4 may transmit the command following the regulation to another measuring device 4.

Although the setting screen 9 is displayed on a display 7a of the device-managing device 7 in the above-mentioned embodiment, the present invention is not limited to this. For example, the setting screen 9 may be displayed on a display of the test automatic managing device 6.

Although the warning screen 8 is displayed on the display 7a of the device-managing device 7 in the above-mentioned embodiment, the present invention is not limited to this. For example, the warning screen 8 may be displayed on the display of the test automatic managing device 6, or each measuring device 4 may be provided with a blinking lamp, and blinking of the lamp may be a warning that can be recognized by the operator.

Although the accumulated operating-time storing unit is provided in the measuring device 4 in the above-mentioned embodiment, the present invention is not limited to this. For example, the accumulated operating-time storing unit may be provided in the device-managing device 7. However, in this case, it is needed to associate the accumulated operating time with the identification ID of the measuring device 4 such that the measuring device 4 can be identified in the device-managing device 7, and to store them in the accumulated operating-time storing unit.

2. Second Embodiment

An exhaust-gas analyzing system (test system) in accordance with a second embodiment of the present invention will be described below with reference to drawings.

Figure 5:
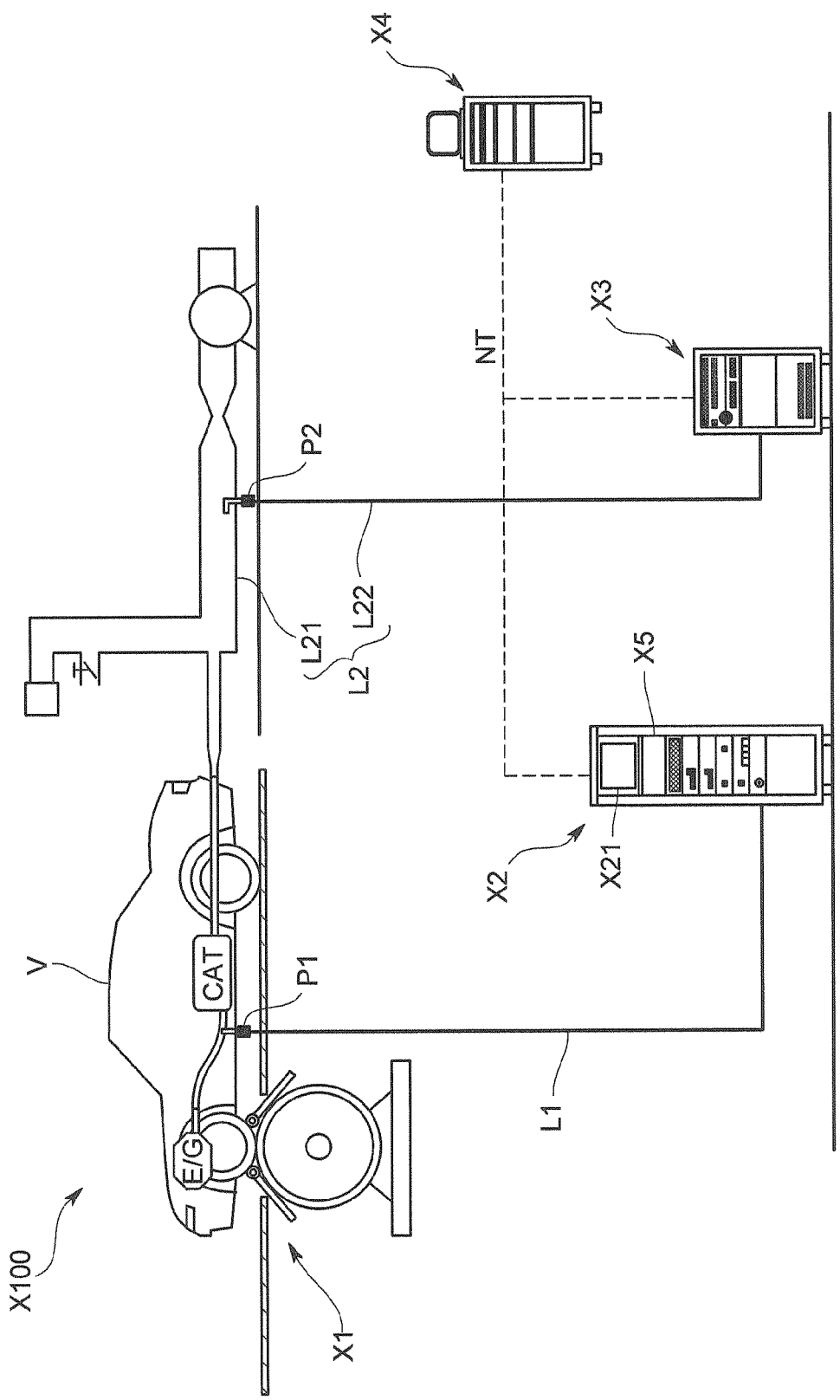
FIG. 5 is a schematic diagram showing a configuration of an exhaust-gas analyzing system in accordance with a second embodiment of the present invention.

An exhaust-gas analyzing system X100 in the second embodiment serves to measure exhaust gas of a vehicle V in a housing called a test cell, and as shown in FIG. 5 illustrating its entire configuration, includes a chassis dynamo device X1 on which the vehicle V is placed as a sample, a first exhaust-gas analyzing device X2 and a second analyzing device X3 that analyze various ingredients contained in the exhaust gas from an engine of the vehicle V, an exhaust-gas flow line L that leads the exhaust gas from the engine to the first exhaust-gas analyzing device X2 and the second analyzing device X3, and a central information processor X4 that receives/transmits data between a dynamo controller (not shown) for controlling the chassis dynamo device X1 and each of the exhaust-gas analyzing devices X2, X3. The exhaust-gas analyzing system X100 further includes an automatic driving mechanism that is installed in a driver's seat of the vehicle V and has a driving arm for mechanically driving an accelerator, a brake, a shift lever, a steering wheel and so on, and an automatic driving mechanism controller that controls the automatic driving mechanism (both are not shown), and operates the driving arm according to an external control signal, thereby having the vehicle V automatically travel on the chassis dynamo device X1.

The exhaust-gas flow line L includes a first exhaust-gas flow line L1 that leads the exhaust gas from the engine to the first exhaust-gas analyzing device X2 without diluting the exhaust gas, and a second exhaust-gas flow line L2 that dilutes the exhaust gas from the engine, which passes a catalyst (CAT) and is discharged from an exhaust pipe (tail pipe), through a diluting tunnel L21 and leads the diluted gas to the second exhaust-gas analyzing device X3.

The first exhaust-gas flow line L1 has an introduction port P1 that introduces the exhaust gas from the engine, one end of which is provided in the exhaust pipe, and the other end of which is connected to a connection port (not shown) of the first exhaust-gas analyzing device X2. The line is a direct sampling line that directly samples the engine exhaust gas.

The second exhaust-gas flow line L2 includes the diluting tunnel L21 that is connected to the exhaust pipe of the vehicle V and dilutes the engine exhaust gas with air, and a diluting sampling line L22 having an introduction port P2 that introduces diluted exhaust gas, one end of which is provided in the diluting tunnel L21 and the other end of which is connected to a connection port (not shown) of the second exhaust-gas analyzing device X3.

The first exhaust-gas analyzing device X2 is a measuring instrument that includes a plurality of gas analyzers having different measurement principles and can continuously measure each of ingredients such as CO, $CO_2$, $O_2$, HC, THC, $CH_4$, NO, $NO_x$ contained in the engine exhaust gas. For example, the first exhaust-gas analyzing device X2 has an infrared-ray gas analyzer using a nondispersive infrared method (NDIR) of measuring the concentration of CO, $CO_2$, HC, and NO, an $NO_x$ meter using chemical luminescence method (CLD) of measuring the concentration of $NO_x$, an $O_2$ meter using a pressure magnetic method (PMD) of measuring the concentration of $O_2$, a THC meter using a heated hydrogen flame ionization detecting method (HFID) of measuring the concentration of THC, and a $CH_4$ meter using a gas chromatograph/hydrogen ionization detector (GC-FID) of measuring the concentration of $CH_4$.

The first exhaust-gas analyzing device X2 includes a computer system configured of a CPU, a memory and so on, and performs a function of communicating a control signal, data and so on with the outside.

The second exhaust-gas analyzing device X3 is a measuring instrument that includes a plurality of gas analyzers having different measurement principles and can continuously measure each of ingredients such as THC, $CH_4$, NO contained in the diluted exhaust gas. For example, the second exhaust-gas analyzing device X3 has an infrared-ray gas analyzer using the nondispersive infrared method (NDIR) of measuring the concentration of NO, a THC meter using the heated hydrogen flame ionization detecting method (HFID) of measuring the concentration of THC, and a $CH_4$ meter using the gas chromatograph/hydrogen ionization detector (GC-FID) of measuring the concentration of $CH_4$.

The second exhaust-gas analyzing device X3 includes a computer system configured of a CPU, a memory and so on, and performs a function of communicating a control signal, data and so on with the outside.

The central information processor X4 is, for example, computer system provided with a CPU, a memory, a communication interface, a display, input means and so on, and has a server function. The central information processor X4 is configured to receive/transmit data from/to each controller and the first and second exhaust-gas analyzing devices X2, X3 via a network NT such as LAN to perform overall control of each controller and the first and second exhaust-gas analyzing devices X2, X3, and data management.

For example, by providing necessary parameters such as vehicle information and a driving mode to the central information processor X4, the chassis dynamo device X1 and the automatic driving mechanism are controlled together via their controllers, the vehicle V (automobile) travels in a desired manner, and the first and second exhaust-gas analyzing devices X2, X3 operate to automatically measure exhaust gas data. Further, the exhaust gas data and driving data are managed by the central information processor X4 in an integrated fashion.

The central information processor X4, each controller and the first and second exhaust-gas analyzing devices X2, X3 need not to be physically separated and dispersed, and as a matter of course, may be integrated partially or wholly.

With such configuration, in the exhaust-gas analyzing system X100 in this embodiment, the first exhaust-gas analyzing device X2 includes an exhaust gas analysis managing device X5 for managing history information of the exhaust-gas analyzing system X100.

Figure 6:
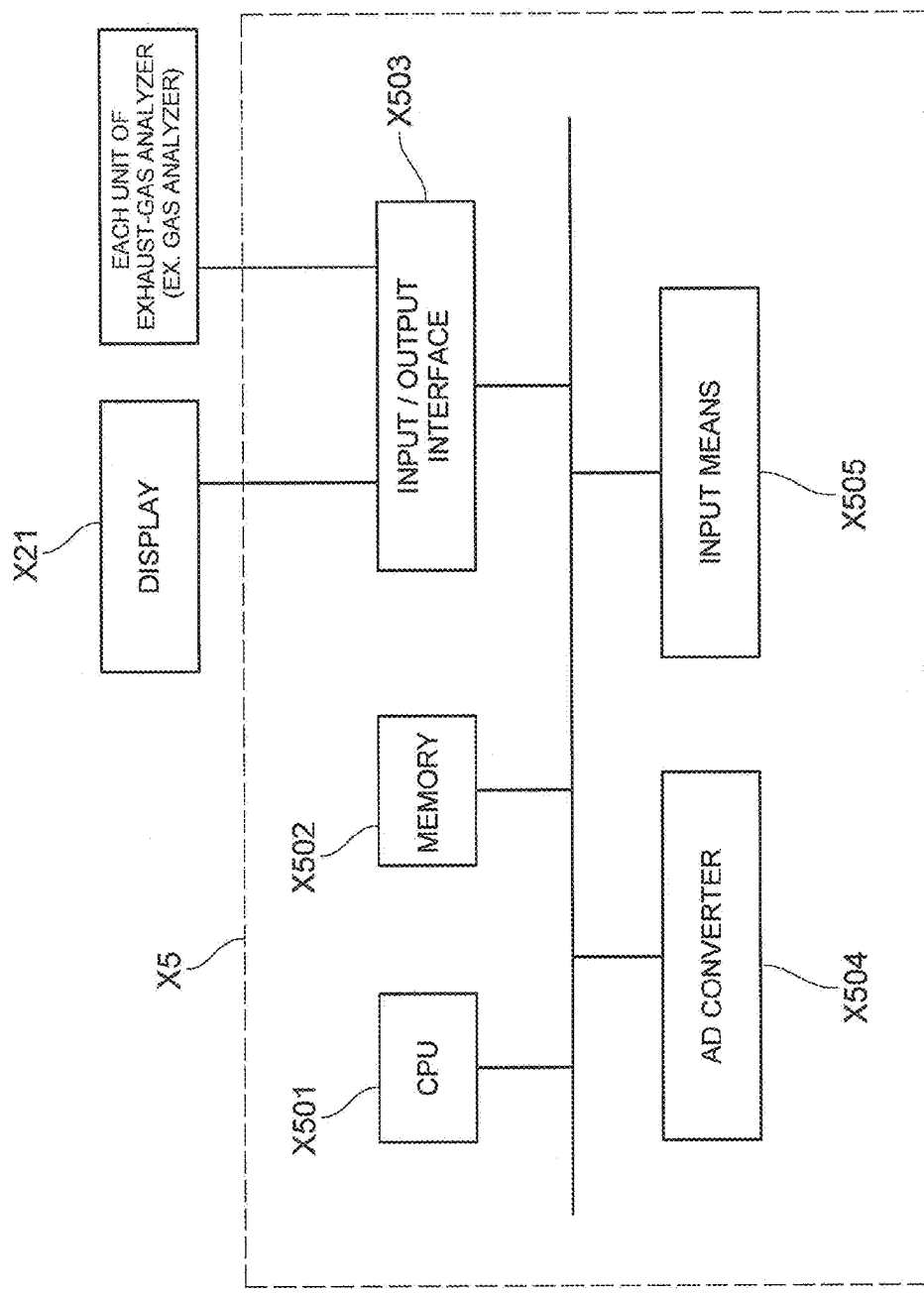
FIG. 6 is an instrument configuration diagram showing a managing device in the second embodiment.
Figure 7:
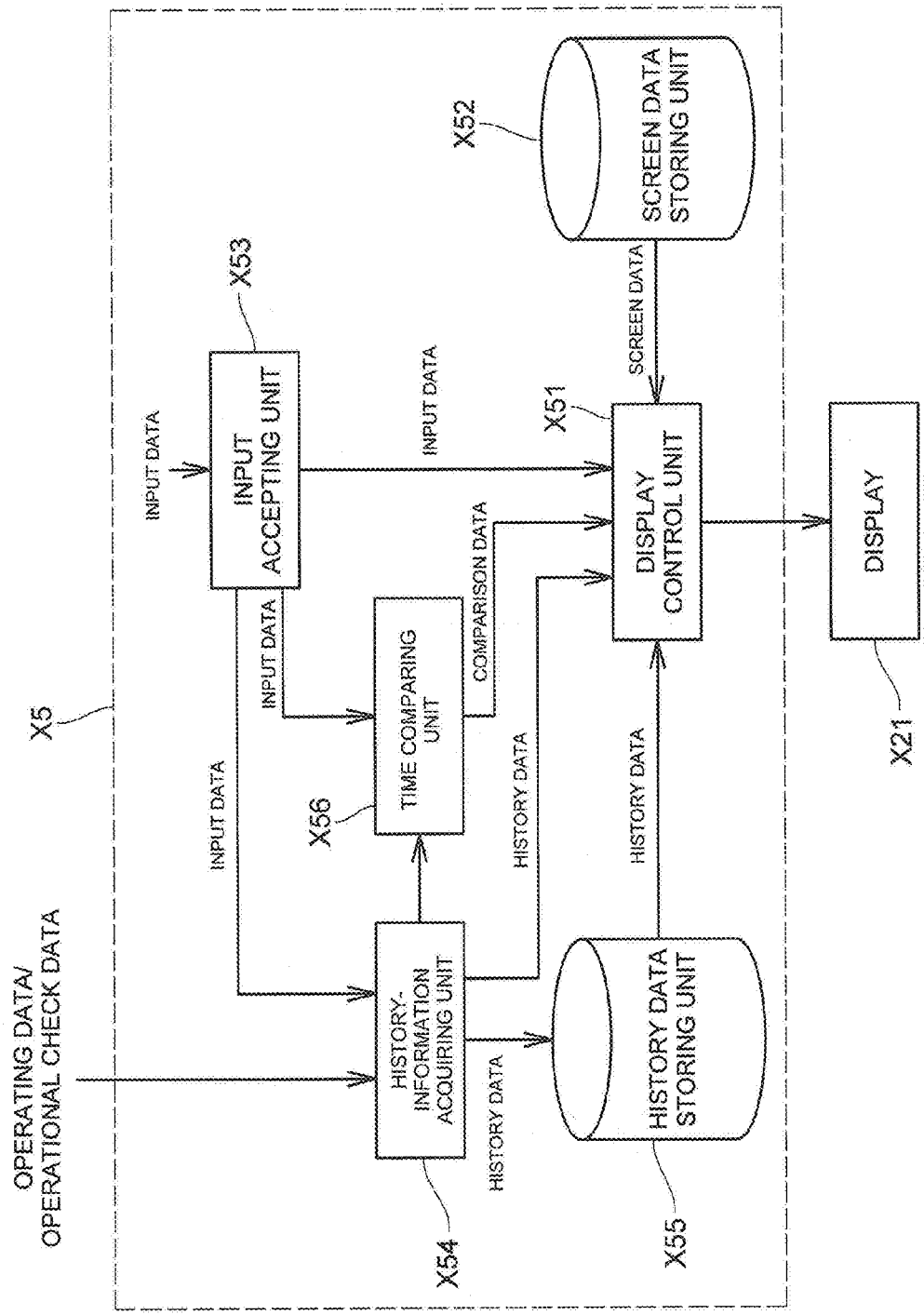
FIG. 7 is a functional configuration diagram showing the managing device in the second embodiment.

The managing device X5 is, as shown in FIG. 6, a general-purpose or dedicated computer including a CPU (X501), a memory X502, an input/output interface X503, an AD converter X504, and input means X505, and the CPU (X501) and the peripheral instruments work together according to a predetermined program stored in a predetermined area of the memory X502, thereby having a display control unit X51, a screen data storing unit X52, input accepting unit X53, history-information acquiring unit X54, a history data storing unit X55, a time comparing unit X56 perform their function as shown in FIG. 7. The managing device X5 uses a display X21 of the first exhaust-gas analyzing device X2, but may have a dedicated display other than the display X21.

The operation of the managing device X5 in conjunction with the function of each of the units X51 to X56 of the managing device X5 will be described with reference to FIG. 7 to FIG. 10.

When the operator selects a history management setting mode by use of the input means X505, the input accepting unit X53 acquires a mode selecting signal and transmits the signal to the display control unit X51. When acquiring the mode selecting signal, the display control unit X51 acquires setting screen data indicating a processing setting screen W1 shown in FIG. 8 to FIG. 10 from the screen data storing unit X52, and displays the setting screen W1 on the display X21. FIG. 8 to FIG. 10 shows the same setting screen W1, but show different display areas varied by use of a scroll bar W11 displayed on a side in the screen.

The setting screen W1 is a screen for setting the instrument and the operational check, which are to be managed, among the plurality of instruments constituting the exhaust-gas analyzing system X100 and a plurality of items of operational check. Specifically, the setting screen W1 has item input columns ("Item Name") S1 for inputting the instrument items indicating the instruments constituting the exhaust-gas analyzing system X100 or operational check items indicating the operational check of the exhaust-gas analyzing system X100.

Examples of the instrument items include the CPU and a tubing pump of the exhaust-gas analyzing devices X2, X3 constituting the exhaust-gas analyzing system X100, and as long as operational data that indicates instrument operation/stop can be acquired from the instrument or the controller controlling the instrument, any instrument item can be set. Examples of the operational check items include basic performance check, linearization check, response check, analyzer check, CO meter interference check, $CO_2$ meter interference check, THC meter $CH_4$ meter relative response/$O_2$ interference check, non-methane cutter efficiency check, $NO_x$ converter efficiency check, leak check, sample line HC hang-up check, $NO_x$ meter quenching check, HC relative response, and as long as operational check data indicating the presence/absence of implementation of the operational check can be acquired, any operational check can be set. In addition, items corresponding to the regulation prescribed in the U.S. EPA (40 CFR Part 1065) can be set in the above-mentioned set item on the setting screen W1 in this embodiment.

The setting screen W1 further includes a setup button ("Item Setup") B1 for setting the instrument item or the operational check item inputted to the item input columns S1, history information display columns (time display columns, "Elapsed") S2 for displaying the operating history (accumulated operating time in this embodiment) of the instruments inputted to the item input columns S1 or the operational check history (elapsed time from completion of the last operational check in this embodiment) of the operational check inputted to the item input columns S1, upper limit value input columns ("Period") S3 for inputting upper limit values (warning set values) of the operating time of the instruments inputted to the item input columns S1 or upper limit values (warning set values) of the elapsed time of the operational check items inputted to the item input columns S1, warning selecting buttons ("Warning") B2 for selecting whether or not a warning is issued when the operating time or the elapsed time exceeds the upper limit value inputted to the upper limit value input column S3, unit selecting buttons ("Unit") B3 for selecting time unit of the upper limit value input columns S3, mode selecting buttons ("Count mode") B4 for selecting various modes that manage the instruments or the operational check inputted to the item input columns S1 (stand-by mode, exhaust gas measurement mode, purge mode, or combination thereof,) and reset buttons ("Reset") B5 for resetting the accumulated operating time or the accumulated interval time displayed in the time display columns S2.

The setting screen W1 further includes a line switching button ("Line") B6 for switching display such that the setting can be made for each exhaust gas flow line (for example, the direct sampling line L1, the diluting sampling line L22, or both ("Common")). The setting screen W1 further includes a finalizing button ("OK") B7 for finalizing the setting inputted to the setting screen W1, and a closing button ("CANCEL") B8 for stopping setting input and closing the setting screen W1.

In this embodiment, as shown in FIG. 8 and FIG. 9, as initial set items, linearization check ("Linearization"), $CO_2$ meter interference check ("$CO_2$ Interference"), $NO_x$ converter efficiency check ("$NO_x$ Efficiency"), leak check ("Leak Check"), sample line HC hang-up check ("HC Hangup Check"), $NO_x$ meter quenching check ("CLA Quenching Check"), HC relative response ("HC Relative Response"), $CO_2$ meter interference check ("$CO_2$ Interference [CFR]"), $NO_x$ converter efficiency check ("$NO_x$ Efficiency [CFR]"), leak check ("Leak Check [CFR]"), sample line HC hang-up check ("HC Hangup Check [CFR]"), $NO_x$ meter quenching check ("CLA Quenching Check [CFR]"), HC relative response ("HC Relative Response [CFR]"), and $O_2$ meter interference check ("$O_2$ Interference Check [CFR]") each according to regulation (CFR) of U.S. EPA, tubing pump of the exhaust-gas analyzing devices X2, X3 ("T.P."), and CPU of the exhaust-gas analyzing devices X2, X3 ("MPU") are previously displayed in the item input columns 51.

As shown in FIG. 9 and FIG. 10, the setting screen W1 includes the plurality of item input columns S1 for inputting a plurality of user-set items other than the initial set items, and the user selects the setup button B1, thereby arbitrarily inputting an item in the item input column S1. Prior to inputting items by the user, "User Definition" is displayed in these item input columns S1.

In the state where the setting screen W1 is displayed, the user inputs a numerical value in the upper limit value input columns S3 by use of the input means X505 such as a keyboard or a mouse to set the upper limit value. In the initial setting state, "Hours" is displayed in the unit selecting buttons B3, and "Hours" can be changed to "Days" by clicking the unit selecting buttons B3. At this time, "Days" is displayed in the unit selecting buttons B3.

Further, the user can switch the mode of acquiring the history information among the stand-by mode ("Stand-by") prior to measurement of the exhaust gas, the exhaust gas measurement mode ("Measure"), the exhaust gas measurement and purge mode ("Measure & Purge") and all mode ("Always") by clicking the mode selecting buttons B4 by use of the input means X505 such as the keyboard or the mouse. By allowing the history information to be acquired in the stand-by mode, in the gas analyzer in which gas flows during stand-by (for example, in an FID meter, N2 gas flows), the timing of maintenance can be determined in consideration of the stand-by state.

When various setting is completed using the setting screen W1, the operator clicks the finalizing button B7 by use of the input means X505 such as the mouse. Accordingly, the various pieces of setting data are accepted by the input accepting unit X53. Then, the various pieces of setting data are transmitted to the history-information acquiring unit X54 and the time comparing unit X56.

When acquiring the setting data, according to the instrument items or the operational check items that correspond to the setting data, the history-information acquiring unit X54 acquires the operating history information of the instruments or the operational check history information of the operational check. Specifically, history-information acquiring unit X54 acquires the operational data indicating the instrument operational information from the instruments or controller for the instruments, management of which is set, and accumulates the operating time of each instrument from the operational data. The history-information acquiring unit X54 acquires the operational check data indicating presence/absence of implementation of the operational check, management of which is set, from the instruments to be checked or the controllers for the instruments, and measures the elapsed time from the last operational check on the basis of the operational check data.

Then, the history-information acquiring unit X54 stores the history data of the accumulated operating time or the elapsed time thus calculated in the history data storing unit X55, and outputs the history data to the time comparing unit X56 and the display control unit X51.

Then, the display control unit X51 displays the accumulated operating time data or the elapsed time data (history data) obtained from the history information acquiring unit X54 in the history information display columns (time display columns) S2 on the setting screen W1.

The time comparing unit X56 compares each upper limit value obtained from the input accepting unit X53 with the accumulated operating time or the elapsed time, and when the accumulated operating time or the elapsed time exceeds the respective upper limit values, outputs comparison data indicating the fact to the display control unit X51. When acquiring the comparison data, the display control unit X51 presents indication that the accumulated operating time or the elapsed time exceeds the respective upper limit values on the setting screen W1 to the user (for example, superimposes the warning screen onto the setting screen W1, or displaying the accumulated operating time or the elapsed time exceeding the upper limit value in a red color).

The managing device X5 is configured to reset the accumulated operating time of the instruments or the elapsed time of the operational check after the maintenance or operational check of the exhaust-gas analyzing system X100 or the instruments constituting the system is performed as described above. Alternatively, the user can reset the accumulated operating time or the elapsed time by clicking the reset buttons B5 displayed on the setting screen W1 by use of the input means X505 such as the mouse.

The exhaust-gas analyzing system X100 in this embodiment thus configured, since the history-information acquiring unit X55 acquires the operating history of the instruments set on the setting screen W1 or the operational check history of the operational check set on the setting screen W1, the operating history of the instruments constituting the exhaust-gas analyzing system X100 or the operational check history of the operational check can be managed, and the instrument or operational check to be managed can be arbitrarily set by the user. Therefore, the exhaust-gas analyzing system X100 enables the user to arbitrarily select the instruments or operational check to be managed, thereby simplifying management of the exhaust-gas analyzing system X100. Since the operating history information includes the accumulated operating time, the amount of gas used in the gas analyzer can be calculated from the accumulated operating time and therefore, running costs can be also managed.

The present invention is not limited to the second embodiment. For example, although the first exhaust-gas analyzing device has the managing device in the second embodiment, the second exhaust-gas analyzing device may have the managing device. Alternatively, since each analyzing device is connected to the central information processor via the network, the central information processor may function as the managing device.

Although the display control unit X51 functions as an informing unit in the second embodiment, an audio output may be separately provided.

Although the history-information acquiring unit X54 calculates the accumulated operating time as the operating history and the elapsed time as the operational check history in the second embodiment, the date and time when the operation is performed or the operational check is made may be acquired.

On the setting screen, the input columns into which the user can make inputs by use of the input means such as the keyboard may be buttons for switching the input items by clicking with the input means such as the mouse, or the buttons for switching the input items by clicking with the input means such as the mouse may be input columns inputted with the input means such as the keyboard.

As a matter of course, the present invention is not limited to the embodiments, and may be variously modified so as not to deviate from the subject matter.

REFERENCE SIGNS LIST

1: Vehicle performance test system (test system)
4: Measuring device (testing devices)
7: Device-managing device
45: Local accumulating unit (accumulated operating-time storing unit)
46: Accumulated operating-time calculating unit
73: Accepting unit
74: Warning generating unit
VH: Vehicle (mobile body)

The invention claimed is:

1. A test system for measuring gas ingredients in sampled intake and/or exhaust gas of an internal-combustion engine, the test system comprising:
    a plurality of measuring devices used for measuring the gas ingredients, wherein each of the plurality of measuring devices includes a plurality of components, wherein each of the plurality of measuring devices is configured to be operable in and switched among at least first and second operational modes in which at least one of the components of the measuring device is set to operate in the first operational mode of the measuring device, and set to not operate while other of the components of the measuring device operate in the second operational mode of the measuring device, and wherein each of the plurality of measuring devices includes a local computer that calculates a measured value indicating a concentration of each ingredient in the sampled gas;
    a device managing device communicably connected to the plurality of measuring devices and configured to manage the plurality of measuring devices;
    a history-information acquiring unit for acquiring, for each of the plurality of measuring devices, operating history information indicating operating history including accumulating operating time of each of the plurality of components, wherein in accumulating the operating time of each of the plurality of components, the history-information acquiring unit accumulates the operating time of the component only in the operational modes for which the component is set to operate and not in the operational modes for which the component is set to not operate; and
    an accepting unit for accepting setting data to set, for each of the plurality of measuring devices, predetermined operational modes, wherein the setting data indicates whether each of the plurality of components of the measuring device should operate.

2. The test system according to claim 1, wherein the history-information acquiring unit is for further acquiring operational check history information indicating operational check history of operational check.

3. The test system according to claim 1, wherein the plurality of measuring devices are provided with the history-information acquiring unit and an accumulated operating-time storing unit for storing accumulated operating time calculated by the history-information acquiring unit.

4. The test system according to claim 1, wherein the device-managing device further includes a warning generating unit for generating a real warning when the accumulated operating time for one of the plurality of components reaches lifetime of the one of the plurality of components, and a preliminary warning when the accumulated operating time reaches a predetermined time prior to the lifetime.

5. The test system according to claim 1, wherein the device-managing device further includes a warning generating unit for generating a real warning when the accumulated operating time for one of the plurality of components reaches lifetime of the one of the plurality of components, and a preliminary warning when the accumulated operating time reaches a predetermined time prior to the lifetime, and wherein the accepting unit accepts setting of the lifetime and/or the predetermined time.

6. The test system according to claim 2, further comprising
    a display control unit displaying a setting screen for setting an instrument with operating history to be managed among the instruments constituting the test system or for setting operational check of the test system with operational check history to be managed, wherein
    the history-information acquiring unit acquires operating history information indicating the operating history of the instrument set on the setting screen, or operational check history information indicating the operational check history of the operational check set on the setting screen.

7. The test system according to claim 2, wherein the operational check history information includes elapsed time from completion of the last operational check.

8. The test system according to claim 6, wherein:
    the setting screen has an upper limit value input column for setting an upper limit value of the accumulated operating time of the set instrument or the elapsed time of the set operational check; and
    the test system further comprising:
    a time comparing unit for comparing the upper limit value set by the upper limit value input column with the accumulated operating time or elapsed time acquired by the history-information acquiring unit; and
    an informing unit for informing that the accumulated operating time or the elapsed time exceeds the upper limit value.

9. The test system according to claim 6, wherein the display control unit displays the operating history information or operational check history information acquired by the history-information acquiring unit on the setting screen.

* * * * *